(12) United States Patent
Chen et al.

(10) Patent No.: US 6,639,074 B2
(45) Date of Patent: Oct. 28, 2003

(54) PROCESS FOR PREPARING AZACYCLOALKANOYLAMINOTHIAZOLES

(75) Inventors: Bang-Chi Chen, Plainsboro, NJ (US); Kyoung S. Kim, North Brunswick, NJ (US); S. David Kimball, East Windsor, NJ (US); Raj N. Misra, Hopewell, NJ (US); Mark E. Salvati, Lawrenceville, NJ (US); Joseph E. Sundeen, Yardley, PA (US); Hai-Yun Xiao, Princeton, NJ (US); Rulin Zhao, Pennington, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/100,129

(22) Filed: Mar. 18, 2002

(65) Prior Publication Data

US 2002/0099217 A1 Jul. 25, 2002

Related U.S. Application Data

(60) Division of application No. 09/746,060, filed on Dec. 22, 2000, now Pat. No. 6,414,156, which is a continuation-in-part of application No. 09/616,627, filed on Jul. 26, 2000, now abandoned, and a continuation-in-part of application No. 09/616,629, filed on Jul. 26, 2000, now Pat. No. 6,214,852, which is a continuation-in-part of application No. 09/464,511, filed on Dec. 15, 1999, now Pat. No. 6,262,096.

(51) Int. Cl.$^7$ .......................... C07D 471/00

(52) U.S. Cl. ............................. 546/63

(58) Field of Search ........................... 546/63

(56) References Cited

U.S. PATENT DOCUMENTS

| | | | |
|---|---|---|---|
| 4,254,260 A | 3/1981 | Takaya | |
| 4,577,016 A | 3/1986 | Alpegiani et al. | |
| 5,418,235 A | 5/1995 | Rendenbach-Mueller et al. | |
| 6,214,852 B1 | 4/2001 | Kim et al. | |
| 2001/0006976 A1 | 7/2001 | Chen et al. | |

FOREIGN PATENT DOCUMENTS

| | | |
|---|---|---|
| EP | 0 275 312 | 7/1988 |
| EP | 0082498 B1 | 11/1989 |
| EP | 0625307 A1 | 11/1994 |
| EP | 0412404 B1 | 1/1996 |
| JP | 8-59669 | 5/1996 |
| WO | W 95/24403 | 9/1995 |
| WO | WO 96/17850 | 6/1996 |
| WO | WO 96/30370 | 10/1996 |
| WO | WO 97/29111 | 8/1997 |
| WO | WO 99/21845 | 5/1999 |
| WO | WO 99/24416 | 5/1999 |
| WO | WO 00/26202 | 5/2000 |
| WO | WO 01/44217 | 6/2000 |
| WO | WO 01/44242 | 6/2000 |
| WO | WO 01/44241 | 4/2001 |

OTHER PUBLICATIONS

T. Ogino et al., "Discovery of FR1115092: A Novel Anti-nephritic Agent"; Bioorg. & Med. Chem. Lett. 8 (1998) 75–80.

K. Tsuji et al., "Synthesis and Effects of Novel Thiazole Derivatives Against Thrombocytopenia"; Bioorg. & Med. Chem. Lett. 8 (1998) 2473–2478.

Baddi et al., "Synthesis and Antimicrobial Activity of Some Ethyl–2–amino/acetamido–5–arylthiothiazole–4–carboxylates and their sulphones: An attempted synthesis of 2–amino acetamido[1]benzothiopyrano[3,2–d]thiazol–9(H)–ones"; Indian J. Chem. 35B (1996) 233–237.

Smith et al., Heterocycles, vol. 37, No. 3, pp. 1865–1872, 1994.

Scott et al., Applied Microbiology, vol. 10, pp. 211–216, 1962.

Hall et al., Journal of Heterocyclic Chemistry, vol. 29, No. 5, pp. 1245–1273, 1992.

Ganellin et al., Journal of Medicinal Chemistry, vol. 38, No. 17, pp. 3342–3350, 1995.

Bellavita et al., Ann. Chim. (Rome) 41, (1951) 194–198.

J. Am. Chem. Soc., vol. LXXI (1949) 4007–4010.

Behringer et al., Ann. Chem. 650 (1961) 179.

Primary Examiner—Robert Gerstl
(74) Attorney, Agent, or Firm—Elliott Korsen; Rena Patel

(57) ABSTRACT

The present invention relates to new, efficient processes for the preparation of 5-(2-oxazolylalkylthio)-2-azacycloalkanoylaminothiazole compounds of formula I

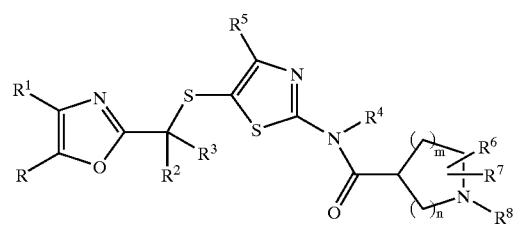

or a pharmaceutically acceptable salt thereof, wherein:

R is alkyl, aryl or heteroaryl;

$R^1$, $R^2$, $R^3$, $R^4$ and $R^5$ are each independently hydrogen, alkyl, aryl or heteroaryl;

$R^6$ and $R^7$ are each independently hydrogen, alkyl, aryl, heteroaryl, halogen, hydroxy or alkoxy;

$R^8$ is hydrogen, alkyl, aryl, heteroaryl, $CONR^9R^{10}$, $COR^{11}$ or $COOR^{12}$;

$R^9$, $R^{10}$, $R^{11}$ and $R^{12}$ are each independently hydrogen, alkyl or aryl;

m equals 0 to 5; and n equals 0 to 5, which are novel, potent inhibitors of cyclin dependent kinases (cdks). The present invention further concerns new key intermediate compounds, a quaternary ammonium salt of formula III' and a 2-oxazolylalkyl derivative of formula IX.

7 Claims, No Drawings

PROCESS FOR PREPARING AZACYCLOALKANOYLAMINOTHIAZOLES

CROSS-REFERENCE TO RELATED U.S. APPLICATIONS

This application is a divisional application of U.S. application Ser. No. 09/746,060, filed on Dec. 22, 2000 now U.S. Pat. No. 6,414,156; which is a continuation-in-part application of (1) U.S. application Ser. No. 09/616,627, filed on Jul. 26, 2000 now abandoned, and (2) U.S. application Ser. No. 09/616,629, filed on Jul. 26, 2000 now U.S. Pat. No. 6,714,852, which are continuation-in-part applications of U.S. application Ser. No. 09/464,511, filed on Dec. 15, 1999 now U.S. Pat. No. 6,262,096.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention concerns new processes for the preparation of 5-(2-oxazolylalkylthio)-2-azacycloalkanoylaminothiazoles and analogs, inhibitors of cyclin dependent kinases.

2. Description of the Related Art

The 5-(2-oxazolylalkylthio)-2-azacycloalkanoylaminothiazole compounds of formula I

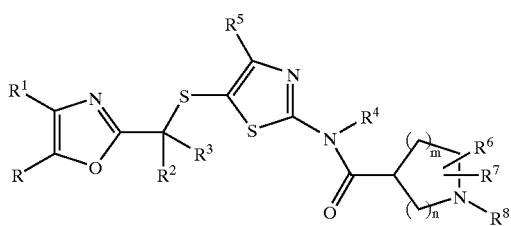

I or a pharmaceutically acceptable salt thereof, wherein:

R is alkyl, aryl or heteroaryl;

$R^1$, $R^2$, $R^3$, $R^4$ and $R^5$ are each independently hydrogen, alkyl, aryl or heteroaryl;

$R^6$ and $R^7$ are each independently hydrogen, alkyl, aryl, heteroaryl, halogen, hydroxy or alkoxy;

$R^8$ is hydrogen, alkyl, aryl, heteroaryl, $CONR^9R^{10}$, $COR^{11}$ or $COOR^{12}$;

$R^9$, $R^{10}$, $R^{11}$ and $R^{12}$ are each independently hydrogen, alkyl or aryl;

m equals 0 to 5; and n equals 0 to 5, are novel, potent inhibitors of cyclin dependent kinases (cdks). They are useful in the therapy of proliferative diseases, for example, cancer, inflammation, autoimmune diseases such as arthritis, viral diseases, fungal diseases, chemotherapy-induced alopecia, neurodegenerative disorders such as Alzheimer's disease and cardiovascular disease. More specifically, the compounds of formula I are useful in the treatment of a variety of cancers such as bladder, breast, colon, kidney, liver and lung cancers.

WO 9924416 and corresponding U.S. Pat. No. 6,040,321 describe the preparation of 5-(2-oxazolylalkylthio)-2-aminothiazoles, key intermediates in the synthesis of 5-(2-oxazolylalkylthio)-2-azacycloalkanoylaminothiazoles of formula I, by reacting 5-acetylthio-2-acetylaminothiazole with a base followed by trapping the thiolate with a 2-oxazolylalkyl halide. Hydrolysis of the resulting 5-(2-oxazolylalkylthio)-2-acetylaminothiazole compounds afforded the 5-(2-oxazolylalkylthio)-2-aminothiazole key intermediates. The requisite 2-oxazolylalkyl halides were prepared by (i) reaction of β-hydroxy amines with α-chloroacyl chlorides followed by oxidation of the resulting β-hydroxy-α-chloroamides and subsequent oxazole ring formation (K. S. Kim et al., WO 9924416, May 20, 1999) or (ii) reaction of α-diazo ketones with α-chloronitriles (K. S. Kim et al., WO 9924416, May 20, 1999; T. Ibata et al., *Bull. Chem. Soc. Japan* 1979, 52, 3597). Although a variety of 5-(2-oxazolylalkylthio)-2-aminothiazoles can be prepared by this method, this process is not amenable to large scale synthesis due to the commercial availability of the starting 5-acetylthio-2-acetylaminothiazole, the use of hazardous α-diazo ketones and expensive chromatographic separation of products.

Reaction of α-halo ketones with azide to give α-azido ketones has been previously reported in the literature (A. Hassner et al., *Angew Chem. Int. Ed. Engl.* 1986, 25, 478; M. G. Nair et al., *J. Med. Chem.* 1980, 23, 899; H.-J. Ha et al., *Synth. Commun.* 1994, 24, 2557). Reaction of α-sulfonyloxy ketones with azide to give α-azido ketones has also been previously reported (T. Patonay et al., *J. Org. Chem.* 1994, 59, 2902; G. A. Revelli et al., *Synth. Commun.* 1993, 23, 1111).

Reduction of α-azido ketones to α-amino ketones has been described in the literature (H.-J. Ha et al., *Synth. Commun.* 1994, 24, 2557; J. P. Sanchez et al., *J. Heterocycl. Chem.* 1988, 25, 469; S. K. Boyer et al., *J. Org. Chem.* 1985, 50, 3408). Reaction of α-amino ketones with α-halo acyl halides to give the corresponding amides has further been described (G. T. Newbold et al., *J. Chem. Soc.* 1948, 1855; G. T. Newbold et al., *J. Chem. Soc.* 1950, 909).

Reaction of alkylthiouronium salts with alkyl halides to give sulfides has been previously reported (H. Chen et al., *Synth. Commun.* 1990, 20,-3313). Reaction of alkylthiols with 5-bromo-2-aminothiazole to give 5-alkylthio-2-aminothiazoles has been reported (J. B. Dickey et al., *J. Org. Chem.* 1959, 24, 187).

BRIEF SUMMARY OF THE INVENTION

This invention concerns new efficient processes for the preparation of 5-(2-oxazolylalkylthio)-2-aminothiazoles. The processes involve new strategies for the preparation of 2-oxazolylalkyl halides and 5-(2-oxazolylalkylthio)-2-aminothiazoles which include the method of making new key intermediate quaternary ammonium salts and 2-oxazolylalkyl sulfide derivatives. This invention further relates to processes for the preparation of 5-(2-oxazolylalkylthio)-2-azacycloalkanoylaminothiazoles and analogs, inhibitors of cyclin dependent kinases.

BRIEF DESCRIPTION OF THE DRAWINGS

Not Applicable

DETAILED DESCRIPTION OF THE INVENTION

The present invention relates to new, more efficient processes for the preparation of 5-(2-oxazolylalkylthio)-2- aminothiazoles with application to the synthesis of 5-(2-oxazolylalkylthio)-2-azacycloalkanoylaminothiazoles and analogs, inhibitors of cyclin dependent kinases. The process generally involves reaction of α-halo ketones II with an azide to give α-azido ketones III. Reduction of III with a reducing reagent gives α-amino ketones IV. From a practical standpoint, safety concerns make this reaction through the azide economically unfeasible.

Alternatively and more advantageously, the α-amino ketones IV are prepared by reaction of α-halo ketones II with a cyclic alkylenetetramine such as hexamethylenetetramine and the like, followed by hydrolysis of the resulting, new quaternary ammonium salt III'. This reaction provides excellent yields of the desired intermediate compound IV, above 90%, yet in a safer manner.

Thereafter, reacting the α-amino ketones IV with an α-halo acyl halide V in the presence of a base or, alternatively, coupling the α-amino ketones IV with an α-halo acid, produces the corresponding amides VI. Then, ring closure of VI with a dehydrating reagent affords 2-oxazolylalkyl halides VII. When a conventional dehydrating reagent such as trihalophosphorus oxide like $POCl_3$ is used, product isolation is difficult due to the formation of large amounts of hydrochloric and phosphoric acids. Thus, the process of the present invention preferably utilizes the Burgess' reagent which produces excellent yields and permits easy, safe product isolation from water.

Subsequent treatment of 2-oxazolylalkyl halides VII with sulfur-containing reagent VIII or VIII' affords new key intermediate compounds, 2-oxazolylalkyl sulfides IX. Coupling of IX with 5-halo-2-aminothiazole X gives 5-(2-oxazolylalkylthio)-2-aminothiazoles XI. Coupling of XI with an azacycloalkanoic acid derivative XII affords thiazolyl amides XIII, which may be deprotected (in the case where P is a protecting group, e.g., Boc) to give 5-(2-oxazolylalkylthio)-2-azacycloalkanoylaminothiazoles I, where $R^7$ is hydrogen, inhibitors of cyclin dependent kinases.

The above-described reactions are illustrated in the below Scheme 1.

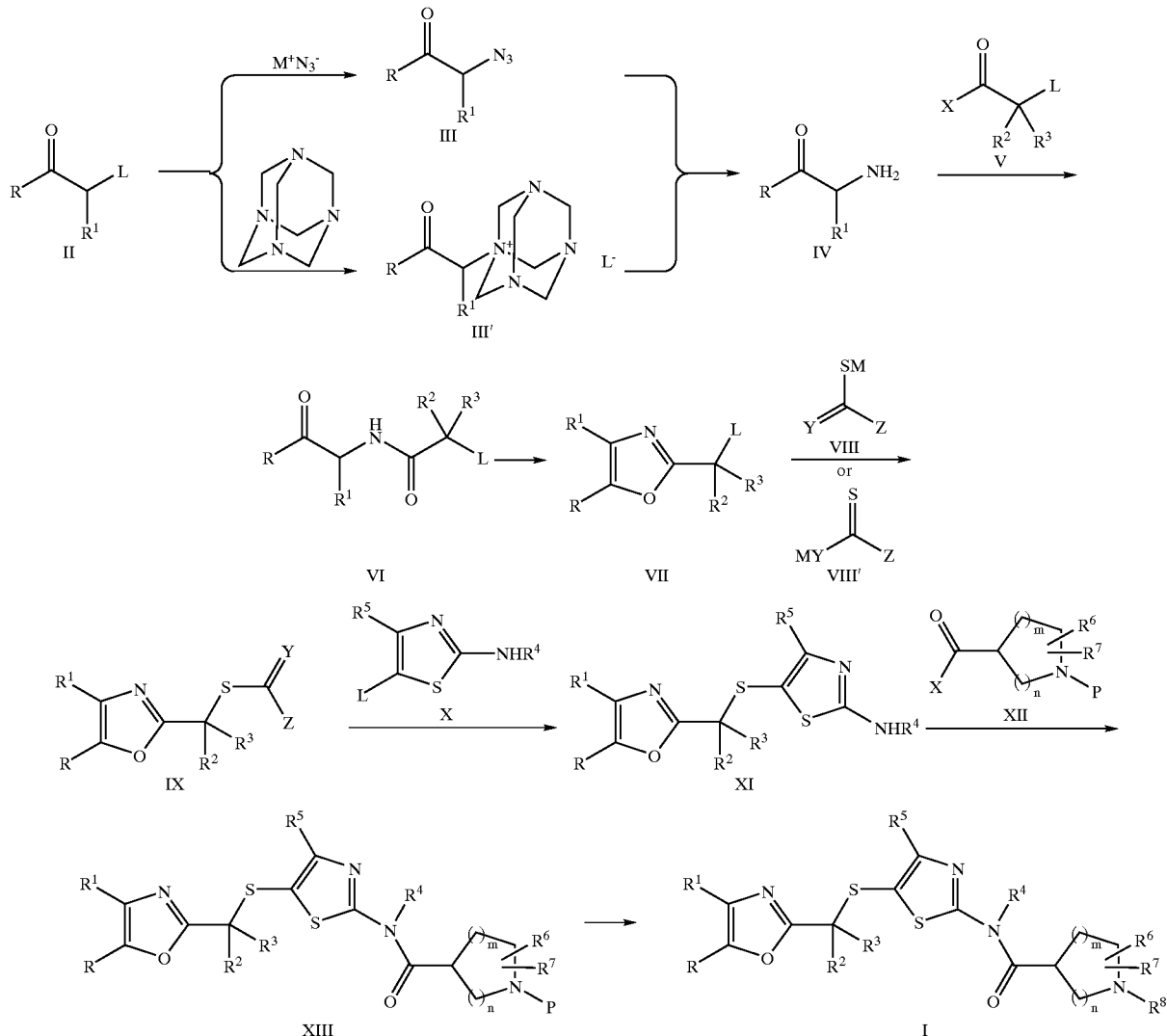

Scheme 1

In formulas I–XIII of Scheme 1, the following terms apply:

R is alkyl, aryl or heteroaryl;

$R^1$, $R^2$, $R^3$, $R^4$ and $R^5$ are each independently hydrogen, alkyl, aryl or heteroaryl;

$R^6$ and $R^7$ are each independently hydrogen, alkyl, aryl, heteroaryl, halogen, hydroxy or alkoxy;

$R^8$ is hydrogen, alkyl, aryl, heteroaryl, $CONR^9R^{10}$, $COR^{11}$ or $COOR^{12}$;

$R^9$, $R^{10}$, $R^{11}$ and $R^{12}$ are each independently hydrogen, alkyl or aryl;

L is halogen or sulfonate ($RSO_2O-$, $CF_3SO_2O-$, etc.);

M is hydrogen, Li, Na, K, Cs or quaternary ammonium ($R_4N$);

X is hydroxy, halogen or acyloxy ($RCOO-$, $ROCOO-$, etc.);

Y is O, S, NH, N-alkyl, N-aryl or N-acyl;

Z is hydrogen, alkyl, aryl, O-alkyl, O-aryl, S-alkyl, S-aryl, $NH_2$, N-alkyl, N-aryl or N-acyl;

P is a nitrogen-protecting group (Boc, Cbz, $R_3Si$, etc.);

m equals 0 to 5; and n equals 0 to 5.

Listed below are definitions of various terms used to describe the compounds involved in the processes of the present invention. These definitions apply to the terms as they are used throughout the specification (unless specifically indicated otherwise) either individually or as part of a larger group. It should be noted that any heteroatom with unsatisfied valences is assumed to have the hydrogen atom to satisfy the valences.

The term "alkyl" or "alk" (i.e., derivative forms of alkyl) refers to optionally substituted straight chain, branched or cyclic monovalent alkane (saturated hydrocarbon) derived radicals containing from 1 to 12 carbon atoms. When substituted, alkyl groups may be substituted with up to four substituent groups at any available point of attachment. Examples of alkyl groups include, but are not limited to, methyl, ethyl, propyl, isopropyl, n-butyl, t-butyl, isobutyl, pentyl, hexyl, isohexyl, heptyl, octyl, nonyl, decyl, undecyl, dodecyl and the like. The alkyl can be optionally substituted with one or more halogens or alkyl groups such as, for example, trifluoromethyl, 4,4-dimethylpentyl, 2,2,4-trimethylpentyl, etc.

The term "aryl" or derivative forms thereof refers to monocyclic or bicyclic aromatic rings, e.g., phenyl, substituted phenyl and the like, as well as groups which are fused, e.g., napthyl, phenanthrenyl and the like, containing from 6 to 30 carbon atoms. An aryl group can thus contain at least one ring having 6 atoms, with up to five such rings being present, containing up to 22 or 30 atoms therein, depending upon optionally alternating (resonating) double bonds between carbon atoms or suitable heteroatoms. Examples of aryl groups include, but are not limited to, phenyl, naphthyl, anthryl, biphenyl and the like.

The term "acyl" refers to the radical $RCO-$, taken alone or in combination, for example, with oxygen, nitrogen, sulfur, etc. The term "halogen" or "halo" refers to chlorine, bromine, fluorine or iodine, with bromine being the preferred halogen.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Exemplary heteroaryl groups include, but are not limited to, thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofurazanyl, etc. The heteroaryl groups can be optionally substituted by one or more groups which include, but are not limited to, halogen, alkyl, alkoxy, hydroxy, carboxy, carbamoyl, alkyloxycarbonyl, trifluoromethyl, cycloalkyl, nitro, cyano, amino, $alkylS(O)_m$ (where m=0, 1 or 2), thiol and the like.

When a functional group is termed "protected," this means that the group is in modified form to preclude undesired side reactions at the protected site. Suitable protecting groups for the compounds involved in the present processes will be recognized from the specification taking into account the level of skill in the art, and with reference to standard textbooks such as T. W. Greene et al., Protective Groups in Organic Synthesis, Wiley, N.Y. (1991).

The term "pharmaceutically acceptable salt" refers to those salts of the biologically active compounds which do not significantly or adversely affect the pharmaceutical properties of the compounds such as, for example, toxicity, efficacy, etc. and include those salts which are conventionally employed in the pharmaceutical industry. Suitable examples of salts include, but are not limited to, those formed with inorganic or organic acids such as hydrochloride, hydrobromide, sulfate, phosphate, etc. Also included, particularly for the intermediate compounds of the invention, are salts which are unsuitable for pharmaceutical utility but which can be employed otherwise, for example, for isolation or purification of free active compounds or their pharmaceutically acceptable salts.

All stereoisomers of the compounds of the instant invention are contemplated, either in admixture or in pure or substantially pure form. The definition of the compounds employed in the processes of the invention embraces all possible stereoisomers and their mixtures. The definition further embraces the racemic forms and the isolated optical isomers having the specified activity. The racemic forms can be resolved by physical methods such as, for example, fractional crystallization, separation or crystallization of diastereomeric derivatives or separation by chiral column chromatography. The individual optical isomers can be obtained from the racemates by conventional methods such as, for example, salt formation with an optically active acid followed by crystallization.

It should be understood that solvates (e.g., hydrates) of the compounds of formula I and the intermediate compounds are also within the scope of the present invention. Methods of solvation are generally known in the art. Therefore, the compounds useful in the processes of this invention may be in the free or hydrate form.

As set forth in Scheme 1, the processes for the preparation of 5-(2-oxazolylalkylthio)-2-azacycloalkanoylaminothiazoles and analogs involve the following transformations:

(a) reacting an α-substituted ketone II such as, for example, an α-halo ketone, with an azide in a suitable solvent or solvent mixtures to give an α-azido ketone III; or, more desirably, (a') reacting an α-substituted ketone II like the α-halo ketone with a cyclic alkylenetetramine such as, for example, hexamethylenetetramine in a suitable solvent or solvent mixtures to give a new quaternary ammonium salt III'.

The α-halo ketone includes α-halo aliphatic and α-halo aromatic ketones. The preferred α-halo ketones are α-halo pinacolones with α-bromo pinacolone most preferred. A sulfonate, for example, $RSO_2O$— (where R is alkyl, aryl or heteroaryl), $CF_3SO_2O$— and the like, may be substituted for the halogen in the α-position. The azides include both metal azides and quaternary ammonium azides. The metal azides are preferred with sodium azide most preferred. Suitable solvent(s) include solvents such as hydrocarbons, ethers, amides, for example, dimethylformamide, ketones, etc., or mixtures thereof, with ketones such as acetone preferred for both reactions (a) and (a').

(b) reacting the α-azido ketone III obtained in step (a) with a reducing reagent in a suitable solvent or solvent mixtures to give an α-amino ketone IV, or, more desirably, (b') reacting the quaternary ammonium salt III' obtained in step (a') with an acid in a suitable solvent or solvent mixtures to give an α-amino ketone IV.

The reducing reagent in reaction (b) includes hydrogen in the presence of a transition metal catalyst such as palladium, trialkyl or triarylphosphines like triphenylphosphine. Hydrogen in the presence of a transition metal catalyst is preferred with hydrogen and palladium over activated carbon most preferred. Suitable solvent(s) in reaction (b) include solvents such as hydrocarbons, ethers, alcohols and the like, or mixtures thereof, with alcohol such as methanol preferred. Alternatively, the reduction reaction can be carried out in the presence of an acidic medium such as, for example, hydrochloric acid in ethanol to give α-amino ketone acid salt which can be isolated as the acid salt or free amine forms.

The acid in reaction (b') includes, but is not limited to, protic acids such as HCl, HBr, HI, $H_2SO_4$, $H_3PO_4$, etc., with HCl preferred. Suitable solvent(s) in reaction (b') include solvents such as hydrocarbons, ethers, alcohols and the like, or mixtures thereof, with alcohol such as ethanol preferred. The α-amino ketone product may be isolated as the salt or free base forms.

(c) reacting (acylating) the α-amino ketone IV or its acid salt obtained in step (b) or (b') with an α-substituted acyl derivative V such as, for example, an α-halo acyl halide, in the presence of a base and in a suitable solvent or solvent mixtures to give an amide VI.

The α-halo acyl halide V includes α-alkyl or aryl substituted or unsubstituted α-halo acyl halide with the latter preferred. The most preferred α-halo acyl halide is α-chloroacetyl chloride. The base used in the reaction includes, but is not limited to, aromatic and aliphatic organic amines with the latter preferred. The most preferred base is triethylamine. Suitable solvent(s) include aprotic solvents such as hydrocarbons, halogenated hydrocarbons, ethers, esters and the like, or mixtures thereof, with halogenated hydrocarbons such as dichloromethane preferred. Alternatively, the reaction can be carried out using an α-substituted acid instead of the α-substituted acyl derivative and then employing a coupling reagent such as a water-soluble diimide like carbodiimide, haloformate, thionyl halide, etc. In either reaction, a sulfonate, for example, $RSO_2O$— (where R is an alkyl, aryl or heteroaryl), $CF_3SO_wO$— and the like, may be substituted for the halogen in the α-position of the α-halo acyl halide or the α-halo acid reactants which are illustrated.

(d) reacting the amide VI obtained in step (c) with a dehydrating reagent in a suitable solvent or solvent mixtures to give the cyclized 2-oxazolylalkyl derivative VII such as, for example, the 2-oxazolylalkyl halide.

Advantageously, the reaction is carried out using (methoxycarbonylsulfamoyl)-triethylammonium hydroxide (Burgess' reagent) as the dehydrating reagent. Suitable solvent(s) include hydrocarbons, halogenated hydrocarbons, ethers and the like, or mixtures thereof. Most preferred is the use of the Burgess' reagent in tetrahydrofuran. Suitable dehydrating reagents also include, but are not limited to, other bases, acids, acid anhydrides and the like, such as, e.g., concentrated sulfuric acid, polyphosphoric acid, etc. Although less conveniently, the dehydrating reagent, for instance, can be trihalophosphorus oxide such as tribromophosphorus oxide or trichlorophosphorus oxide, alone or with a solvent like toluene.

(e) reacting the 2-oxazolylalkyl derivative VII obtained in step (d) with a sulfur-containing reagent VIII or VIII' in a suitable solvent or solvent mixtures to give 2-oxazolylalkyl sulfide IX, a new key intermediate compound.

The sulfur-containing reagent includes N-substituted or unsubstituted thioureas, thio acids or salts such as thioacetic acid or its salt, xanthic acids or salts such as ethylxanthic acid potassium salt. Unsubstituted thiourea is preferred. Suitable solvent(s) include hydrocarbons, halogenated hydrocarbons, ethers, esters, amides, alcohols and the like, or mixtures thereof, with alcohol such as methanol or ethanol preferred.

(f) reacting the 2-oxazolylalkyl sulfide IX obtained in step (e) with a 5-halo-2-aminothiazole X in the presence of a base and in a suitable solvent or solvent mixtures to give 5-(2-oxazolylalkylthio)-2-aminothiazole XI.

The 5-halo-2-aminothiazole includes 4,N-substituted or unsubstituted 5-halo-2-aminothiazoles with 5-bromo-2-aminothiazole preferred. A suitable base includes, but is not limited to, metal hydroxide, metal alkoxides, metal carbonates and aqueous amines such as ammonium hydroxide. Sodium hydroxide is preferred. Suitable solvent(s) include solvents such as hydrocarbons, halogenated hydrocarbons, ethers, esters, amides, alcohols and the like, or mixtures thereof, with halogenated hydrocarbons such as dichloromethane preferred.

(g) reacting the 5-(2-oxazolylalkylthio)-2-aminothiazole XI obtained in step (f) with an azacycloalkanoic acid derivative XII in the presence of a coupling reagent in a suitable solvent or solvent mixtures to give thiazolyl amide XIII.

The azacycloalkanoic acid derivative includes N-protected derivatives, for example, N-protected isonipecotic acid or N-protected nipecotic acid. The preferred nitrogen-protecting groups are Boc, Cbz, silicon derivatives and the like with Boc being the most preferred. The coupling reagent includes, but is not limited to, water-soluble carbodiimides, haloformates and the like, with carbodiimides such as alkylcarbodiimides being preferred. Suitable solvent(s) include solvents such as hydrocarbons, halogenated hydrocarbons, ethers, esters, amides, etc., or mixtures thereof, with halogenated hydrocarbons such as dichloromethane preferred.

(h) reacting the thiazolyl amide XIII obtained in step (g) with a deprotecting reagent in a suitable solvent or solvent mixtures to give a desired 5-(2-oxazolylalkylthio)-2-azacycloalkanoylaminothiazole I (where $R^7$ is hydrogen).

The choice of the deprotecting reagent is based on the nature of the protecting group (P). For the Boc protecting group, the preferred deprotecting reagent is an acid such as hydrochloric acid or trifluoroacetic acid and suitable solvent(s) for such deprotecting reaction include solvents such as hydrocarbons, halogenated hydrocarbons, ethers, esters, amides and the like, or mixtures thereof, with halogenated hydrocarbons such as dichloromethane preferred.

The starting compounds of Scheme 1 are commercially available or may be prepared by methods known to one of ordinary skill in the art.

To further illustrate Scheme 1, a process to make 5-(5-t-butyl-2-oxazolylmethylthio)-2-azacycloalkanoylaminothiazoles and analogs thereof, for example, starts with reaction of α-bromo pinacolone II (R=Bu-t, $R^1$=H, L=Br) with sodium azide to give an α-azido pinacolone III (R Bu-t, $R^1$=H). Reduction of α-azido pinacolone III (R=Bu-t, $R^1$=H) with a reducing reagent gives α-amino pinacolone IV (R=Bu-t, $R^1$=H). Alternatively and more desirably, the α-amino pinacolone IV (R=Bu-t, $R^1$=H) is prepared by reaction of α-bromo pinacolone II (R=Bu-t, $R^1$=H, L=Br) with hexamethylenetetramine followed by hydrolysis of the resulting quaternary ammonium salt III' (R=Bu-t, $R^1$=H, L=Br). Coupling of α-amino pinacolone IV (R=Bu-t, $R^1$=H) with an α-chloroacetyl chloride V ($R^2$=$R^3$=H, L=X=Cl) produces amide VI (R=Bu-t, $R^1$=$R^2$=$R^3$=H, L=Cl). Ring closure of VI with a dehydrating reagent affords 5-t-butyl-2-oxazolylmethyl chloride VII (R=Bu-t, $R^1$=$R^2$=$R^3$=H, L=Cl). Treatment of VII with sulfur-containing reagent VIII or VIII' such as thiourea affords 5-t-butyl-2-oxazolylalkyl sulfide IX (R=Bu-t, $R^1$=$R^2$=$R^3$=H, Y=NH, Z=$NH_2$). Coupling of IX with 5-bromo-2-aminothiazole X ($R^4$=$R^5$=H, L=Br) gives 5-(5-t-butyl-2-oxazolylmethylthio)-2-aminothiazole XI (R=Bu-t, $R^1$=$R^2$=$R^3$=$R^4$=$R^5$=H). Coupling of XI with N-Boc azacycloalkanoic acid XII (X=OH, $R^6$=$R^7$=H, m=0, n=2, P=Boc), affords thiazolyl amide XIII (R=Bu-t, $R^1$=$R^2$=$R^3$=$R^4$=$R^5$=$R^6$=$R^7$=H, m=0, n=2, P=Boc), which after deprotection, gives rise to the desired 5-(5-t-butyl-2-oxazolylmethylthio)-2-azacycloalkanoylaminothiazole I (R=Bu-t, $R^1$=$R^2$=$R^3$=$R^4$=$R^5$=$R^6$=$R^7$=H, m=0, n=2), or an analog thereof.

The present invention further includes two novel key intermediate compounds of formulae III' and IX which have been produced from the new processes to synthesize 5-(2-oxazolylalkylthio)-2-azacycloalkanoylaminothiazoles of formula I.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the non-limiting examples which follow below.

EXAMPLE 1

A. Preparation of α-Azido-pinacolone

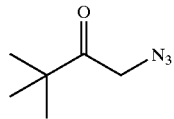

α-Bromo-pinacolone (199.07 g, 1.1115 mol, 1 eq) was combined in 1.785 L of acetone with sodium azide (93.9 g, 1.4444 mol, 1.3 eq). The reaction was stirred at room temperature for 27.5 hours. The resulting slurry was filtered and washed with acetone (3×150 mL). The filtrate was concentrated in vacuo to provide 154.3 g (98.4%) of the title compound. HPLC 83.85% at 2.57 minutes (Phenomenex Inc., Torrance, Calif., 5 μm C18 column 4.6×50 mm, 10–90% aqueous methanol over 4 minutes containing 0.2% phosphoric acid, 4 mL/min, monitoring at 220 nm).

EXAMPLE 2

A' Preparation of α-Hexamethylenetetramino-pinacolone Bromide

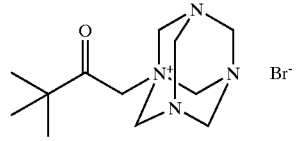

α-Bromo-pinacolone (179 g, 1 mol, 1 eq) was combined in 2 L of acetone with hexamethylenetetramine (154.21 g, 1.1 mol, 1.1 eq) and the reaction stirred under $N_2$ at room temperature for 26 hours. The resulting slurry was filtered, the filter cake was washed with ether. (3×50 mL) and dried in vacuo at 50° C. overnight to provide 330 g (100%) of the title compound containing 7% hexamethylenetetramine. HPLC R.T.=0.17 min (Phenomenex Inc., 5 μm C18 column 4.6×50 mm, 10–90% aqueous methanol over 4 minutes containing 0.2% phosphoric acid, 4 mL/min, monitoring at 220 nm).

EXAMPLE 3

B. Preparation of α-Amino-pinacolone Hydrochloride

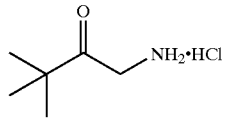

α-Azido-pinacolone (128.5 g, 0.911 mol) was combined in 4.2 L of methanol with 77.1 mL of concentrated HCl and 15.42 g of 10% Pd/C. The reaction mixture was stirred under hydrogen for 1.5 hours. The catalyst was removed by filtration. The solvent was distilled to give a wet solid. The residual water was azeotropically removed with isopropanol (2×500 mL). Tert-butyl methyl ether (300 mL) was added and the resulting slurry was stirred, filtered, washed with t-butyl methyl ether (3×100 mL) and dried to give 131.0 g (95.5%) of the title compound.

EXAMPLE 4
B'. Preparation of α-Amino-pinacolone Hydrochloride

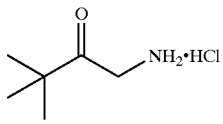

α-Hexamethylenetetramino-pinacolone bromide (400 g, 1.254 mol, 1 eq) was combined in 2 L of ethanol with 12 N aqueous HCl (439 mL, 5.26 mol, 4.2 eq). The reaction was stirred at 75° C. for 1 hour and then allowed to cool to room temperature, the resulting slurry filtered, the filtrate concentrated in vacuo and isopropyl alcohol was added. The solution was filtered again. Addition of 1.2 L of ether caused the desired material to precipitate from solution. The material was filtered, washed with ether (2×300 mL), and dried in vacuo at 50° C. overnight to provide 184.1 g (97%) of the title compound.

EXAMPLE 5
C. Preparation of α-N-(2-Chloroacetylamino)-pinacolone

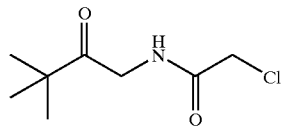

The title compound of Example 4 (130.96 g, 0.8637 mol, 1 eq) was dissolved in 3.025 L of $CH_2Cl_2$ under $N_2$ at $-5°$ C. Triethylamine (301 mL, 2.16 mol, 2.5 eq) was added, followed by chloroacetyl chloride (75.7 mL, 0.450 mol, 1.1 eq) in 175 mL of $CH_2Cl_2$. The resulting slurry was stirred at $-5$ to $-10°$ C. for 2 hours. Water (1.575 L) was added, followed by 175 mL of concentrated HCl. The organic phase was washed a second time with 1.75 L of 10% aqueous HCl, and then with 500 mL of water. The organic phase was dried over $Na_2SO_4$ and concentrated in vacuo to provide 155.26 g (93.8%) of the title compound. HPLC R.T.=2.27 min (Phenomenex Inc., 5 μm C18 column 4.6×50 mm, 10–90% aqueous methanol over 4 minutes containing 0.2% phosphoric acid, 4 mL/min, monitoring at 220 nm).

EXAMPLE 6
D. Preparation of 5-(t-Butyl)-2-oxazolylmethyl Chloride

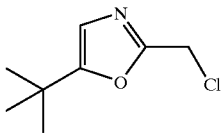

The title compound of Example 5 (180.13 g, 0.9398 mol, 1 eq) was combined with phosphorus oxychloride (262 mL, 2.8109 mol, 3 eq) under $N_2$. The reaction was heated at 105° C. for 1 hour, the mixture was cooled to room temperature, and quenched with 1.3 kg of ice. The aqueous phase was extracted with ethyl acetate (1 L, then 2×500 mL). The organic extracts were washed with saturated aqueous $NaHCO_3$ (4×1 L) which was back-extracted several times with ethyl acetate. The organic phases were combined, washed with saturated aqueous $NaHCO_3$ (500 mL) followed by saturated aqueous NaCl (300 mL), dried over $MgSO_4$, and concentrated in vacuo to give a brown oil. The crude material was distilled under high vacuum at 100° C. to provide 155.92 g (96%) of the title compound. HPLC R.T.=3.62 min (Phenomenex Inc., 5 μm C18 column 4.6×50 mm, 10–90% aqueous methanol over 4 minutes containing 0.2% phosphoric acid, 4 mL/min, monitoring at 220 nm).

Alternatively, the title compound of Example 5 (10.0 g, 52.17 mmol, 1 eq.) in 50 mL of tetrahydrofuran (THF) was combined with (methoxycarbonylsulfamyl)-triethylammonium hydroxide (Burgess' reagent, 105.70 mmol, 2.03 eq., generated in situ from 9.2 mL of chlorosulfonyl isocyanate, 4.4 mL of methanol and 14.8 mL of triethylamine in 100 mL THF). The reaction was heated to 45° C. for 1.5 hours. After cooling to room temperature, the reaction was quenched with water (50 mL). The organic layer was separated and washed with saturated $NaHCO_3$ (2×50 mL) and water (50 mL), dried over $MgSO_4$ and passed through a small silica gel plug. The solvent was removed to give an oil which was taken up in a mixture of 15 mL heptane and 90 mL of t-butyl methyl ether, and then washed with 0.2 N HCl (2×25 mL), saturated brine (25 mL) and dried ($MgSO_4$). Filtration and removal of solvent gave 10.9 g of the title compound.

EXAMPLE 7
E. Preparation of 5-(t-Butyl)-2-oxazolylmethyl Thiouronium Hydrochloride

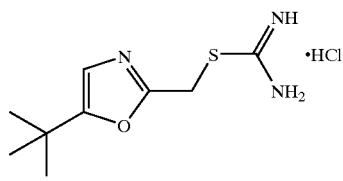

The title compound of Example 6 (1.77 g, 10.2 mmol, 1.02 eq) was combined with thiourea (0.76 g, 9.98 mmol, 1 eq) under $N_2$ in 10 mL of absolute ethanol. The reaction was heated at reflux for 1.5 hours. The mixture was cooled to room temperature and concentrated in vacuo. Trituration of the resulting crude material with t-butyl methyl ether provided 2.32 g (93%) of the title compound. HPLC R.T.=2.05 min (Phenomenex Inc., 5 μm C18 column 4.6×50 mm, 10–90% aqueous methanol over 4 minutes containing 0.2% phosphoric acid, 4 mL/min, monitoring at 220 nm); $^1$H NMR ($d_6$-DMSO): δ9.48 (s, 3H), 6.85 (s, 1H), 4.73 (s, 2H), 1.24 (s, 9H).

EXAMPLE 8
F. Preparation of 5-[5-(t-Butyl)-2-oxazolylmethylthio]-2-aminothiazole

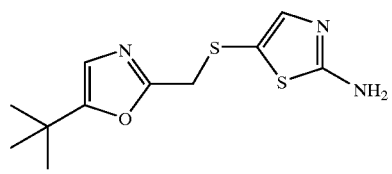

The title compound of Example 7 (1.25 g, 5 mmol, 1 eq) was added to a mixture of NaOH (3.0 g, 75 mmol, 15 eq), water (10 mL), toluene (10 mL) and tetrabutylammonium sulfate (50 mg, 0.086 mmol, 0.017 eq). 5-Bromo-2-aminothiazole hydrobromide (1.70 g, 5 mmol, 1 eq) was added and the reaction was stirred at room temperature for 14.5 hours. The mixture was diluted with water and extracted twice with ethyl acetate, the organic extracts washed with water (4×10 mL), dried over $MgSO_4$ and concentrated in vacuo to provide 1.1 g (82%) of the title compound. HPLC 86.3% at 2.75 min (Phenomenex Inc., 5 μm C18 column 4.6×50 mm, 10–90% aqueous methanol over 4 minutes containing 0.2% phosphoric acid, 4 mL/min, monitoring at 220 nm); $^1$H NMR (CDCl$_3$): δ6.97 (s, 1H), 6.59 (s, 1H), 5.40 (br s, 2H), 3.89 (s, 2H), 1.27 (s, 9H).

EXAMPLE 9

G. Preparation of 5-[5-(t-Butyl)-2-oxazolylmethylthio]-2-[(N-t-butoxycarbonyl)-azacycloalkanoyl]aminothiazole

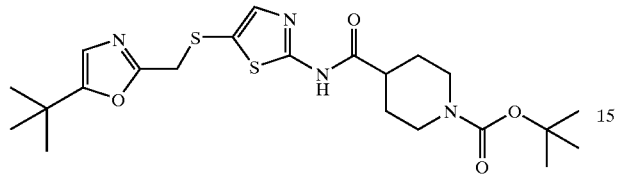

The title compound of Example 8 (9.6 g, 35.6 mmol) was dissolved in N,N-dimethylformamide (36 mL) and CH$_2$Cl$_2$ (100 mL), to which was added 1-(3-dimethylaminopropyl)-3-ethylcarbodiimide hydrochloride (13.8 g, 72 mmol, 2 eq), N-t-butoxycarbonyl-azacycloalkanoic acid (12.6 g, 55 mmol, 1.5 eq), and 4-(dimethylamino)pyridine (2 g, 16 mmol, 0.45 eq). The clear reaction mixture became cloudy as it was stirred at room temperature for 3.5 hours. Water (300 mL) and ethyl acetate (200 mL) were added and the resulting precipitate was removed by filtration. The filtrate was extracted with ethyl acetate, the organic extracts dried over MgSO$_4$ and concentrated in vacuo to provide a yellow solid which was combined with the precipitate obtained by filtration. The solid was boiled in a mixture of ethanol, acetone and water for 20 minutes, filtered, washed with an ethanol/water mixture and dried to give 16.6 g (97%) of the title compound.

EXAMPLE 10

H. Preparation of 5-[5-(t-Butyl)-2-oxazolylmethylthio]-2-(azacycloalkanoyl)amino-thiazole hydrochloride

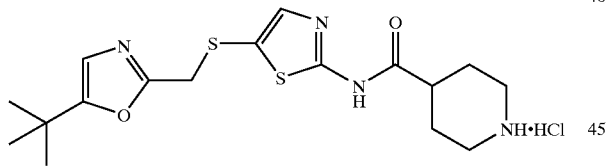

The title compound of Example 9 (16.6 g) was dissolved in 150 mL of CH$_2$Cl$_2$, trifluoroacetic acid (30 mL) was added dropwise, and the mixture was stirred at room temperature for 2 hours. The reaction was concentrated in vacuo, diluted with water (300 mL), cooled in ice, made basic with sodium hydroxide, and the resulting solid filtered and recrystallized from ethanol, water and methanol to provide 11.2 g (83%) of the title compound as a yellow solid. The white solid hydrochloride could be obtained by addition of 18 mL of 1N aqueous HCl to 7 g of this material in methanol. MS: 381 [M+H]$^+$; HPLC: 100% at 3.12 min (YMC S5 ODS column 4.6×50 mm, 10–90% aqueous methanol over 4 minutes containing 0.2% phosphoric acid, 4 mL/min, monitoring at 220 nm).

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:

1. A process for the preparation of a compound having the formula III'

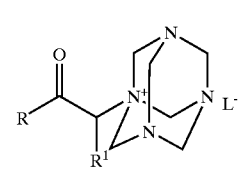

or a salt thereof, wherein:

R is alkyl;

R$^1$ is hydrogen, alkyl, aryl or heteroaryl; and

L is halogen or a sulfonate;

with the proviso that when R is CH$_3$, R$^1$ cannot be H;

which comprises reacting an α-substituted ketone having the formula II

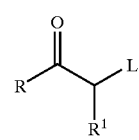

wherein:

R, R$^1$ and L are as described hereinabove;

with a cyclic alkylenetetramine in a suitable solvent or solvent mixture to form the compound of formula III'.

2. The process as recited in claim 1, wherein R is t-butyl.

3. A compound having the formula III'

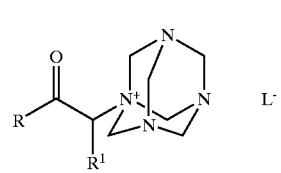

or a salt thereof, wherein:

R is alkyl;

R$^1$ is hydrogen, alkyl, aryl or heteroaryl; and

L is halogen or a sulfonate.

4. The compound as recited in claim 3, wherein R is t-butyl.

5. The compound as recited in claim 4, wherein R$^1$ is hydrogen.

6. The compound as recited in claim 5, wherein L is halogen.

7. The compound as recited in claim 6, α-hexamethylenetetramino-pinacolone bromide.

* * * * *